United States Patent [19]
Abe et al.

[11] Patent Number: 5,752,493
[45] Date of Patent: May 19, 1998

[54] APPARATUS FOR CONTROLLING A HEATER FOR HEATING AN AIR-FUEL RATIO SENSOR

[75] Inventors: Shinichi Abe, Aichi-gen; Toshio Inoue, Susono, both of Japan

[73] Assignee: Toyota Jidosha Kabushiki Kaisha, Aichi, Japan

[21] Appl. No.: 877,277

[22] Filed: Jun. 17, 1997

[30] Foreign Application Priority Data

Jun. 24, 1996 [JP] Japan ............... 8-162936

[51] Int. Cl.⁶ .................. F02D 41/14; G01N 27/04
[52] U.S. Cl. ........................... 123/686; 123/697
[58] Field of Search .................... 123/679, 686, 123/689, 697; 73/23, 32; 204/406, 425

[56] References Cited

U.S. PATENT DOCUMENTS

| | | | |
|---|---|---|---|
| 4,694,809 | 9/1987 | Nakano et al. | 123/697 X |
| 4,889,098 | 12/1989 | Suzuki et al. | 123/697 X |
| 4,993,392 | 2/1991 | Tanaka et al. | 123/697 X |
| 5,067,465 | 11/1991 | Yamasaki et al. | 123/697 X |

FOREIGN PATENT DOCUMENTS

| | | |
|---|---|---|
| 60-214251 | 10/1985 | Japan . |
| 61-155744 | 7/1986 | Japan . |
| 1-158335 | 6/1989 | Japan . |
| 1-265148 | 10/1989 | Japan . |

*Primary Examiner*—Tony M. Argenbright
*Attorney, Agent, or Firm*—Kenyon & Kenyon

[57] ABSTRACT

A heater control apparatus for an air-fuel ratio sensor that is capable of supplying optimum power, regardless of the coolant temperature of an internal combustion engine at the engine start-up, is provided. When the internal combustion engine is started, a switching element 122 is continuously held at ON state, to continuously supply power to a heater 112 of the air-fuel ratio sensor 11. The duty cycle of the switching element is controlled so that the heater temperature is maintained at 1100° C., after the heater resistance, which is calculated from the voltage applied to the heater and the current flowing through the heater, has reached a predetermined value, and so that a sensing element 111 is maintained at a temperature of 710° C., after the air-fuel ratio sensor was activated. In performing the control, the power supplied to the heater is increased by adding an auxiliary power calculated as a function of the coolant temperature detected by a coolant temperature sensor 142 and the time elapsed since the engine was started up, thereby preventing an excessive temperature rise of the heater and a delay in the activation of the air-fuel ratio sensor.

6 Claims, 9 Drawing Sheets

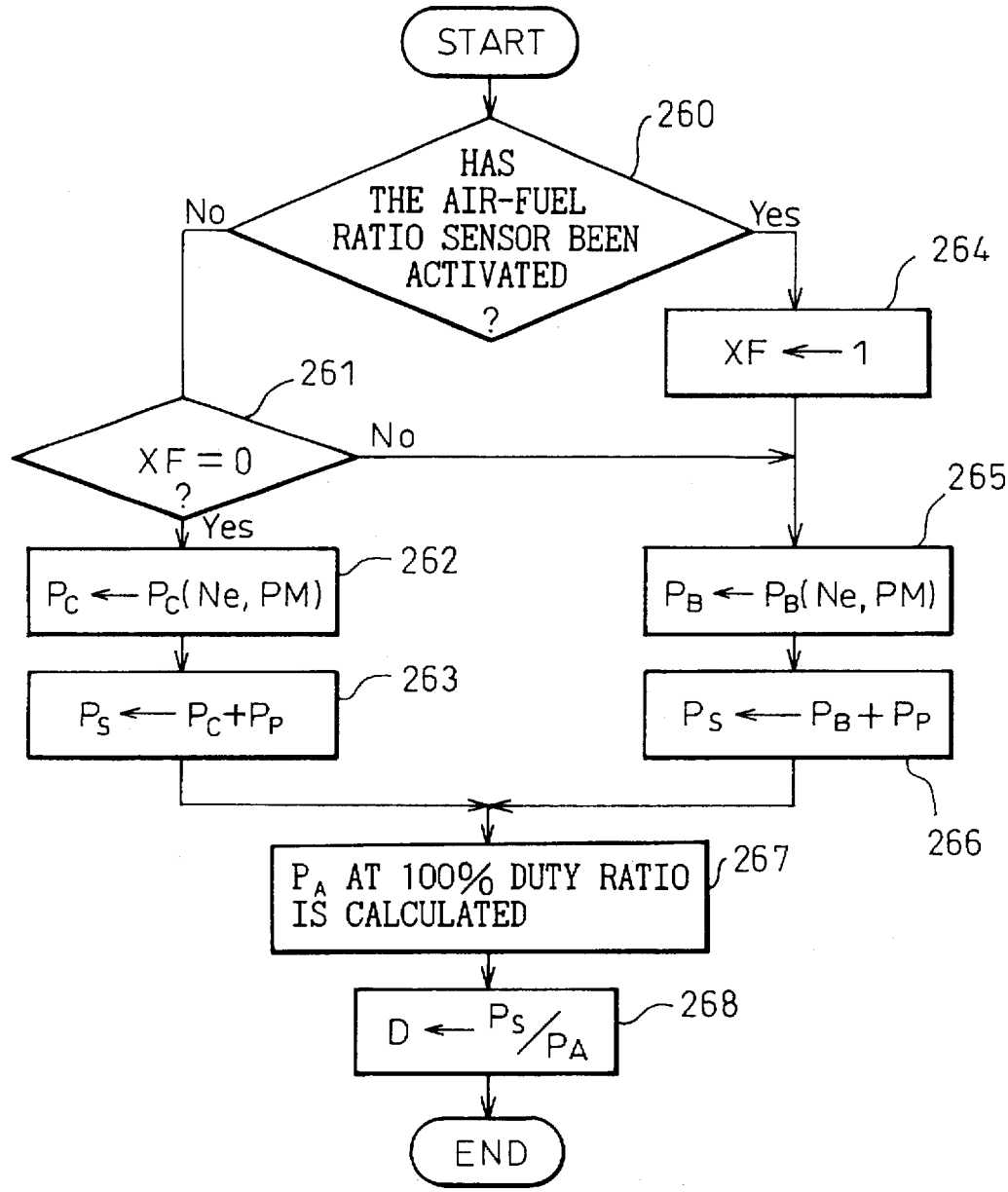

APPARATUS FOR CONTROLLING A HEATER FOR HEATING AN AIR-FUEL RATIO SENSOR

BACKGROUND OF THE INVENTION

1. Field of the Invention

The present invention relates to an apparatus for controlling a heater for heating an air-fuel ratio sensor, and more particularly to an apparatus for controlling a heater, for heating an air-fuel ratio sensor, which is capable of preventing an excessive temperature rise of the heater and a delay in the activation of the air-fuel ratio sensor, regardless of the engine coolant temperature at an engine start-up.

2. Prior Art

It is well known to control an air-fuel ratio of mixture supplied to a cylinder of an internal combustion engine to a target air-fuel ratio (for example, to the stoichiometric air-fuel ratio) by adjusting a basic injected amount of fuel in accordance with the oxygen density in the exhaust gas to improve automotive exhaust emission, specific fuel consumption and drivability.

For such an air/fuel ratio control, it is essential to detect the amount of oxygen contained in the exhaust gas. Since an output voltage of the air-fuel ratio sensor is affected not only by oxygen concentration but also by the temperature of the air-fuel ratio sensor itself, the air-fuel ratio sensor must be heated by a heater and be maintained at a first temperature of about 650° C. or above.

However, because the temperature is affected by the exhaust gas temperature, an apparatus for controlling the heater which controls a basic electric power supplied to the heater in accordance with the engine operating condition, and increases the basic electric power to accelerate the air-fuel ratio sensor before activation, has been proposed (See Unexamined Japanese Patent Application No. 1-158335).

The base power to be supplied to the heater is controlled so that the air-fuel ratio sensor or the heater are maintained at respective optimum temperatures while the engine is operating after the engine has completely warmed up, that is, after the temperature of the exhaust gas flowing around the air-fuel ratio sensor has risen sufficiently. Therefore, an apparatus that increases an electric power in accordance with the engine coolant temperature having correlation with the exhaust gas temperature, to compensate for a shortage of heating power at a low temperature condition while the engine is being warmed up has been proposed (see Unexamined Japanese Patent Publication No. 1-147138).

According to the above-mentioned apparatus, the increasing amount of the electric power is determined based on the engine coolant temperature detected by a coolant temperature sensor.

However, if the coolant temperature detected by the coolant temperature sensor is 20° C., for example, an electric power required to heat the air-fuel ratio sensor when the engine is started under low temperature conditions (for example, −20° C.) is different from that when the engine is started under normal temperature conditions (for example, 15° C.). It is, therefore, not appropriate to determine the increasing amount of the electric power based on the coolant temperature.

Namely, when the increased amount of the electric power is determined in accordance with the coolant temperature so that the temperature of the heater is maintained at an optimum temperature after the engine is started from a low temperature condition, activation of the air-fuel sensor is delayed by a shortage of the increasing amount after the engine is started from a normal temperature condition.

Conversely, when the increased amount of the electric power is determined so that the temperature of the heater is maintained at an optimum temperature after the engine is started from a normal temperature condition, the temperature of the heater rises excessively after the engine is started from a low temperature condition.

SUMMARY OF THE INVENTION

To solve the above-mentioned problems, it is an object of the present invention to provide an apparatus, for controlling a heater for heating an air-fuel ratio sensor, which is capable of preventing an excessive temperature rise of the heater and a delay in the activation of the air-fuel ratio sensor, by supplying optimum power to the heater regardless of the engine coolant temperature at the engine start.

According to the first invention, an apparatus is provided for controlling a heater for heating an air-fuel ratio sensor installed in an exhaust pipe for detecting air-fuel ratio of exhaust gas, comprising: an operating condition detecting means for detecting an operating condition of an internal combustion engine; a base electric power determining means for determining a base electric power in accordance with the operating condition detected by said operating condition detecting means; an auxiliary electric power determining means for determining an auxiliary electric power which becomes less as a coolant temperature of the engine detected by said operating condition detecting means becomes lower, and becomes less as time the elapsed after the engine was started becomes longer; and an electric power controlling means for controlling an electric power supplied to the heater by adding the auxiliary electric power determined by said auxiliary electric power determining means to the base electric power determined by said base electric power determining means.

According to this apparatus, the electric power supplied to the heater is increased in accordance with not only the coolant temperature, but also the time elapsed after the engine was started up.

According to the second invention, said electric power controlling means continuously supplies the electric power before the resistance of the heater reaches a fixed resistance after the engine was started, and controls the electric power by adding the auxiliary electric power determined by said auxiliary electric power determining means to the base electric power determined by said base electric power determining means after the resistance of the heater reaches a fixed resistance.

According to the third invention, said auxiliary electric power determining means determines an auxiliary electric power so that it becomes less as a coolant temperature of the engine detected by said operating condition detecting means becomes lower, and becomes less as time elapsed after the resistance of the heater reached a fixed resistance becomes longer.

BRIEF DESCRIPTION OF THE DRAWINGS

FIG. 3 is a flowchart of a power calculating subroutine;

DETAILED DESCRIPTION OF THE PREFERRED EMBODIMENTS

Figure 1:
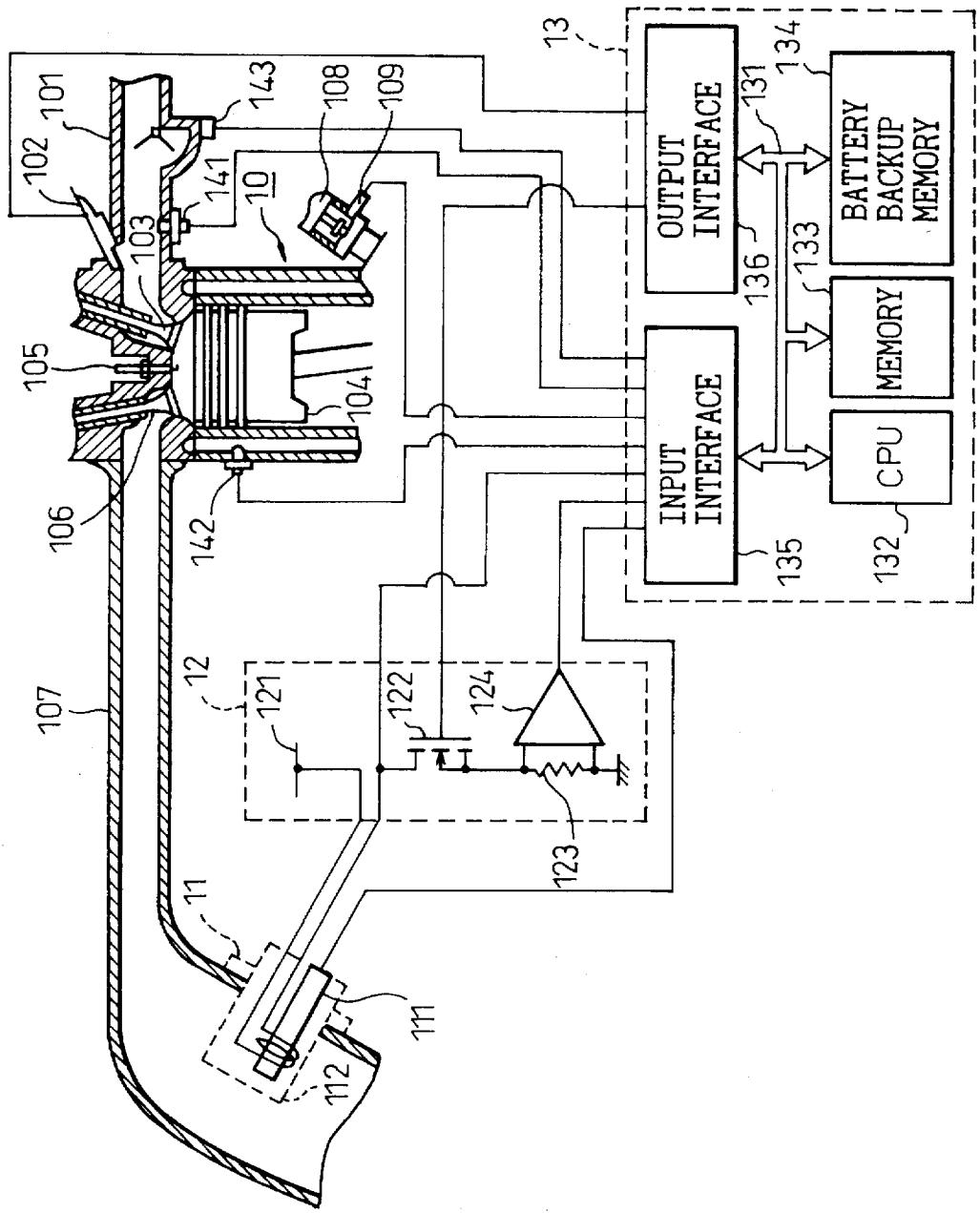
FIG. 1 is a diagram showing the configuration of an apparatus for controlling a heater for heating an air-fuel ratio sensor according to the present invention.

FIG. 1 is a diagram showing the configuration of an apparatus for controlling a heater for heating an air-fuel ratio sensor according to the present invention. Air flowing through an intake manifold 101 and fuel injected from a fuel injector valve 102 are mixed together, and the air-fuel mixture is supplied through an intake valve 103 into an internal combustion engine 10.

The air-fuel mixture is compressed by a piston 104, and is ignited by a spark plug 105 when the piston 104 has reached near top dead center, producing power to push the piston 104 downward. After burning, the exhaust gas is discharged through an exhaust valve 106 into an exhaust manifold 107.

A speed of the internal combustion engine 10 is detected by an engine speed sensor 109 incorporated in a distributor 108.

A limiting-current type air-fuel ratio sensor 11 for detecting residual oxygen concentration in the exhaust gas is mounted in the exhaust manifold 107. The air-fuel ratio sensor 11 consists of a sensing element 111 and a heater 112 for heating the sensing element 111.

The heater 112 is powered from a drive circuit 12 which consists of a power supply 121, a switching element 122, a current detection resistor 123, and a buffer amplifier 124.

More specifically, the heater 112, the switching element 122, and the current detection resistor 123 are connected in series between the power supply 121 and ground (vehicle chassis). A current flowing through this series connection is detected by measuring the voltage developed across the current detection resistor 123 through the buffer amplifier 124.

There is also provided a controller 13 which is a microcomputer system comprising a CPU 132, a memory 133, a battery backup memory 134, an input interface 135, and an output interface 136, interconnected by a bus 131.

Data stored in the battery backup memory 134 will not be lost though the vehicle key is turned off (that is, though the ignition key is pulled out), unless the memory is disconnected from the battery.

Not only the engine speed sensor 109 and the sensing element 111 of the air-fuel ratio sensor 11, but also an intake pressure sensor 141 mounted in the intake manifold 141, a coolant temperature sensor 142, and an inlet air flow rate sensor 143 are connected to the input interface 134.

The output interface 135 outputs a valve opening command to the fuel injector valve 102 as well as on/off commands to the switching element 122.

Figure 2:
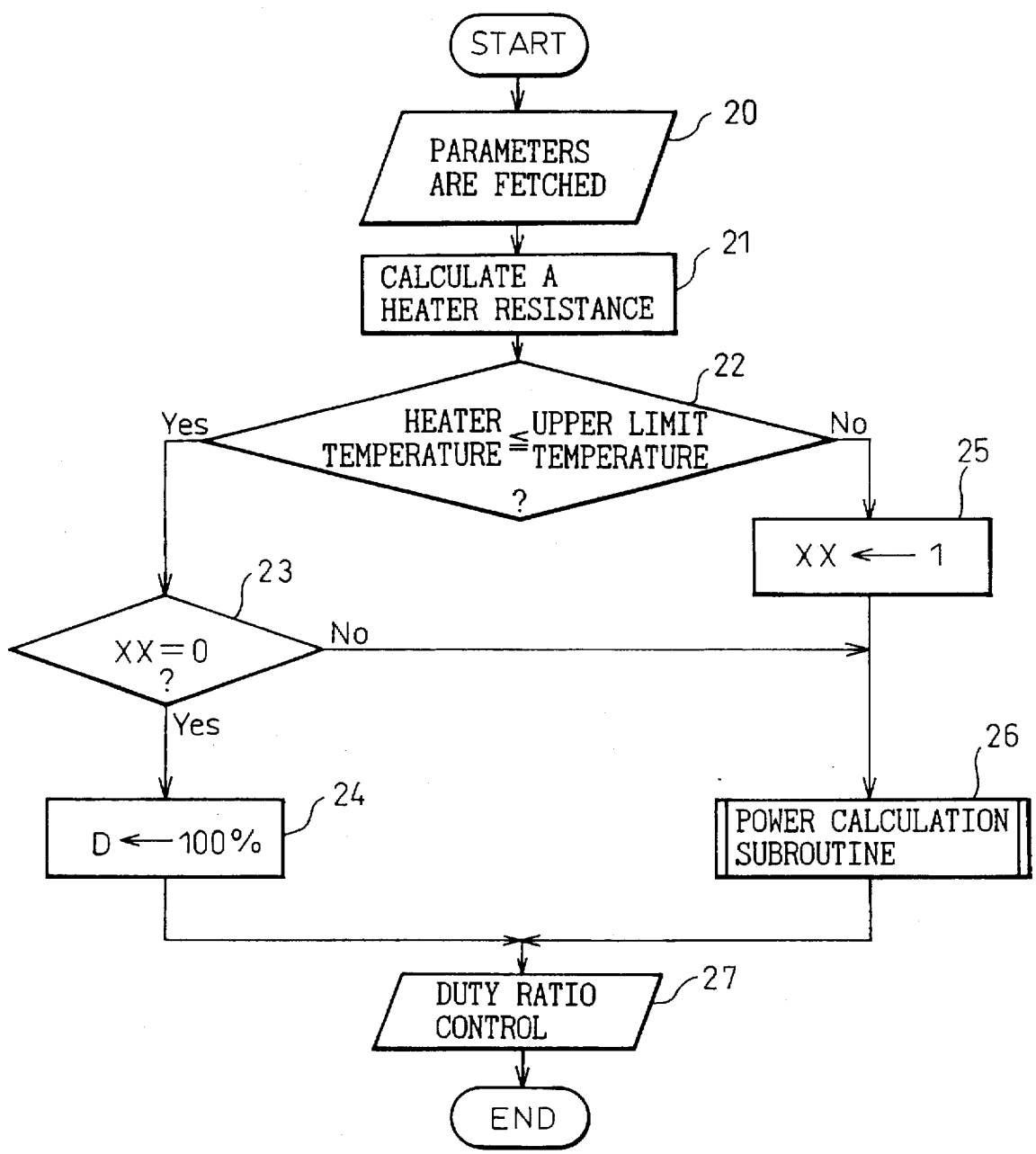
FIG. 2 is a flowchart of a first heater control routine.

FIG. 2 is a flowchart illustrating a first heater control routine executed in the controller 13. This routine is executed every prescribed interval.

At step 20, an engine speed $N_e$, an intake pressure $P_M$, a voltage $V_h$ at the downstream of the heater, a current $I_h$ flowing through the heater, and coolant temperature $T_{hw}$ are fetched.

At step 21, a heater resistance $R_h$ is calculated from a battery voltage $V_B$, a heater downstream voltage $V_h$, and a heater current $I_h$, using the equation below.

$$R_h = (V_B - V_h)/I_h$$

At step 22, it is determined whether or not the heater temperature is less than or equal to a predetermined upper limit temperature (for example, 1100° C.), that is, whether or not the heater resistance $R_h$ is less than or equal to an upper limit resistance value corresponding to the upper limit temperature.

When the determination at step 22 is affirmative, that is, when the heater temperature is not higher than the upper limit temperature, the control proceeds to step 23 to determine whether or not a flag XX, indicating that the heater temperature has not exceeded the upper limit temperature after the engine was started, that is, whether or not the heater temperature has ever risen above the upper limit temperature after the engine was started is "0". Here, the flag XX was initialized to 0 by a not shown initialization routine when the engine was started.

When the determination at step 23 is affirmative, that is, when the heater temperature has never risen above the upper limit temperature since the engine was last started, then the control proceeds to step 24, where duty cycle D is set to 100% to expedite activation of the air/fuel ratio sensor 11. The control then proceeds to step 27.

Conversely, when the determination at step 22 is negative, that is, when the heater temperature is above the upper limit temperature, the control proceeds to step 25, where the flag XX is set to 1, and then the control proceeds to step 26. Namely, when the determination at step 23 is negative, that is, when the heater temperature has risen above the upper limit temperature since the engine was last started, the control proceeds to step 26.

At step 26, a power calculation subroutine is executed, and then the control proceeds to step 27. At step 27, the switching element 122 is controlled using the duty cycle D determined at step 24 or step 26, and then, the routine is terminated.

FIG. 3 is a flowchart illustrating the power calculating subroutine executed at step 26. At step 260, it is determined whether or not the air-fuel ratio sensor 11 has been activated. Whether or not the air/fuel ratio sensor 11 has been activated can be determined, for example, by checking whether or not the output response curve of the air/fuel ratio sensor 11 has exceeded a predetermined length.

When the determination at step 260 is negative, that is, when the air-fuel ratio sensor 11 has not yet been activated, the control proceeds to step 261 where the flag XF, indicating that the air-fuel ratio sensor 11 has never been activated after the engine was started, is "0". When the flag XF is 0, the control proceeds to step 262. Note, the flag XF was previously initialized to 0 by a not shown initialization routine.

At step 262, according to a heater temperature 1100° C. map which is a function of the engine speed $N_e$ and the intake pressure $P_M$, a base power $P_C$ for 1100° C. that is required to maintain the heater temperature at 1100° C., that is, a high limit temperature that does not deteriorate a lifetime of the heater, is obtained from the following formula.

$$P_C = P_C(N_e, P_M)$$

The 1100° C. map is used to determine the base power $P_C$ required to maintain the heater temperature at 1100° C.

when the engine has been completely warmed up and the exhaust gas temperatures is sufficiently high. While an engine warms-up, however, the exhaust gas is still low, and it is not possible to maintain the heater temperature at 1100° C. by using only the 1100° C. base power $P_C$. Accordingly, at step 263, an auxiliary power $P_P$ is added to the 1100° C. base power $P_C$ to obtain a supplied power $P_S$ as shown in the following formula.

$$P_S = P_C + P_P$$

Then, the process proceeds to step 267.

The auxiliary power $P_P$ is calculated in an auxiliary power calculating routine which will be described later.

Conversely, when the determination at step 260 is affirmative, that is, when it is determined that the air-fuel ratio sensor 11 has been activated, the flag XF is set to 1 in step 264, and the control proceeds to step 265. Note, when the determination at step 261 is negative, that is, when the air-fuel ratio sensor 11 has been activated since the engine was started, the control also proceeds to step 265.

At step 265, according to an element temperature 710° C. map which is a function of the engine speed $N_e$ and intake pressure $P_M$, a base power $P_B$ for 710° C. that is required to control the temperature to 710° C. to maintain it at at least 650° C., considering manufacturing error of the air-fuel ratio sensing element 111 is obtained.

$$P_B = P_B(N_e, P_M)$$

The 710° C. map is used to determine the base power $P_B$ for 710° C. required to maintain the temperature of the sensing element 111 of the air-fuel ratio sensor at 710° C. when the engine has been completely warmed up and the exhaust gas temperature is sufficiently high. While an engine warms-up, however, the exhaust gas is still low, and it is not possible to maintain the temperature of the sensing element 111 at 710° C. by using only the 710° C. base power $P_B$. Accordingly, at step 266, an auxiliary power $P_P$ is added to the 710° C. base power $P_B$ to obtain a supplied power $P_S$ as shown in the following formula.

$$P_S = P_B + P_P$$

Then, the control proceeds to step 267.

The auxiliary power $P_P$ is calculated by an auxiliary power calculation routine described later.

A supplied power $P_A$, when the duty is set to 100%, is obtained at step 267, the duty cycle D is calculated by the equation below at step 268, and this subroutine is terminated.

$$D = P_S / P_A$$

Figure 4A:
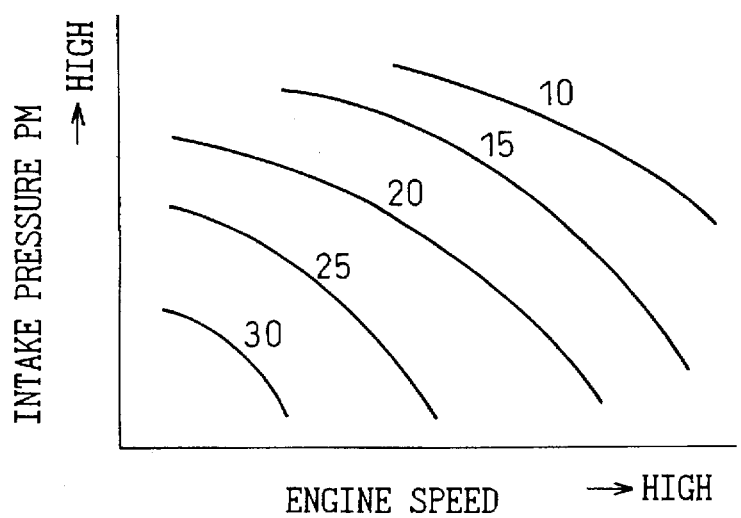
FIGS. 4A and 4B are diagrams showing base power calculating maps.
Figure 4B:
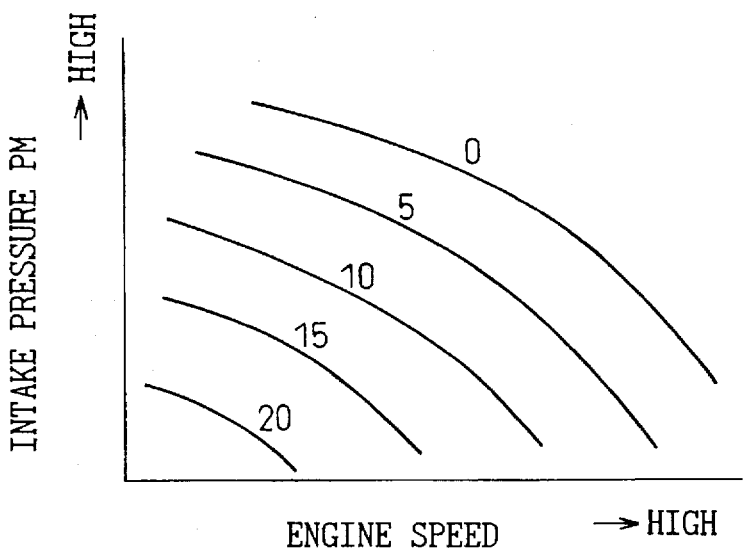

FIGS. 4A and 4B show the base power calculation maps, where the engine speed $N_e$ is plotted along the abscissa and the intake pressure $P_M$ along the ordinate. The parameter is the base power.

Note, FIG. 4A shows the heater temperature 1100° C. map, and FIG. 4B shows the element temperature 710° C. map. For the same engine speed and the same intake pressure, the 1100° C. base power $P_C$ is larger than the 710° C. base power $P_B$.

Figure 5:
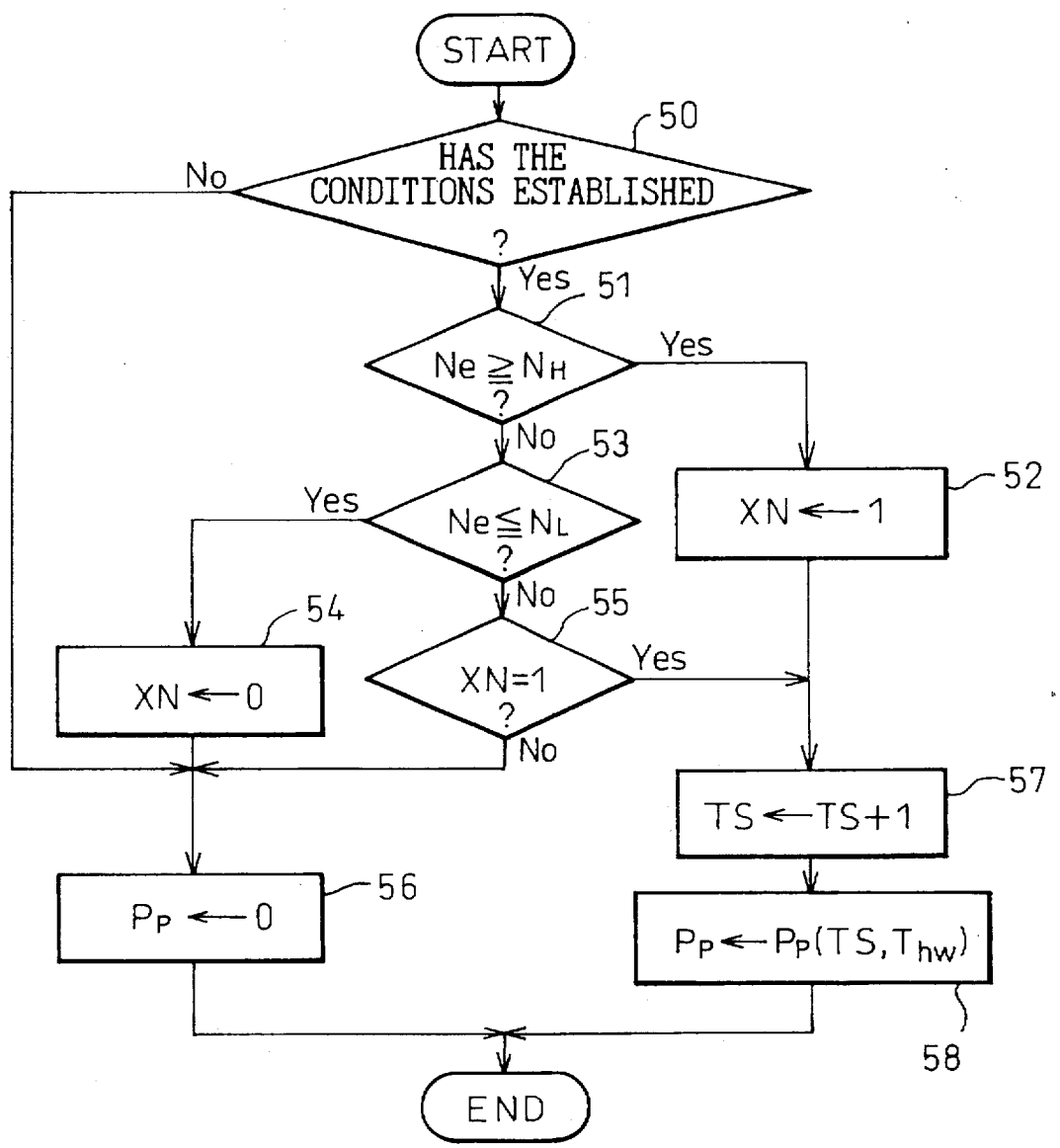
FIG. 5 is a flowchart of a first auxiliary power calculation routine.

FIG. 5 is a flowchart illustrating a first auxiliary power calculating routine executed at the controller 13. This routine is executed every prescribed interval.

At step 50, it is determined whether or not conditions for calculating the auxiliary power are established.

The conditions for calculating the auxiliary power include the following:

(1) The heater temperature is not too high.

(2) Heater diagnostic results are normal.

When all the conditions are established, it is determined that the conditions for calculating the auxiliary power are established, and the control proceeds to step 51.

Step 51 through step 55 concern the processing to determine whether or not an engine cranking has been completed, that is, it is determined whether or not the engine speed $N_e$ has exceeded a cranking completion engine speed $N_H$ (for example, 400 rpm). To stabilize the determination, hysteresis is applied.

At step 51, it is determined whether or not the engine speed $N_e$ has exceeded the cranking completion engine speed $N_H$, and when the determination at step 51 is affirmative, that is, when the engine speed $N_e$ has exceeded the cranking completion engine speed $N_H$, a cranking completion flag XN is set to 1 at step 52, and the control proceeds to step 57.

When the determination at step 51 is negative, the control proceeds to step 53, where it is determined whether or not the engine speed $N_e$ is less than or equal to cranking incompletion engine speed $N_L$ (for example, 200 rpm).

When the determination at step 53 is affirmative, that is, when the engine speed $N_e$ is less than or equal to the cranking incompletion engine speed $N_L$, the cranking completion flag XN is set to 0 at step 54, and the control proceeds to step 56.

When the determination at step 53 is negative, that is, when the engine speed $N_e$ is above the cranking incompletion engine speed $N_L$ but not above the cranking completion engine speed $N_H$, the control proceeds to step 55 to determine whether or not the cranking completion flag XN is 1. If the determination is negative, the control proceeds to step 56; if the determination is affirmative, the control proceeds to step 57.

At step 56, the correction power $P_P$ is set to 0.0, and the routine is terminated. Note, when the determination at step 50 is negative, that is, when the conditions for calculating the auxiliary power are not established, the control also proceeds to step 56.

A counter TS indicating the elapsed time after engine start-up is incremented at step 57, and the auxiliary power $P_P$ is calculated at step 58.

Because the auxiliary power $P_P$ is to prevent the air-fuel ratio sensing element 111 from being cooled by the exhaust gas when the temperature of the exhaust gas is low, the auxiliary power $P_P$ is theoretically determined as a function of the exhaust gas temperature. However, since it is difficult to directly detect the temperature of the exhaust gas, the auxiliary power $P_P$ is determined based on the coolant temperature having correlation with the exhaust gas temperature in the present invention.

Figure 6A:
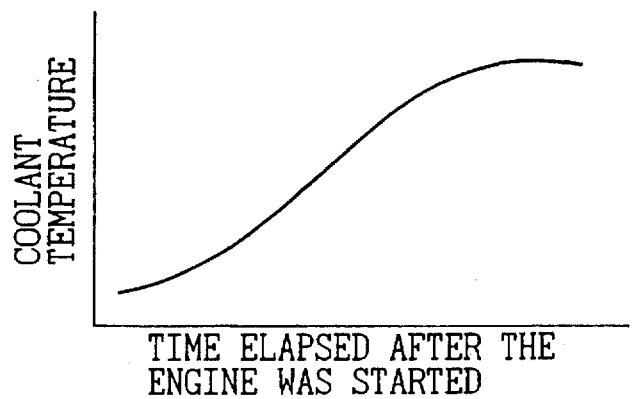
FIGS. 6A, 6B and 6C are diagrams for explaining the relationship between an exhaust gas temperature and a coolant temperature.
Figure 6B:
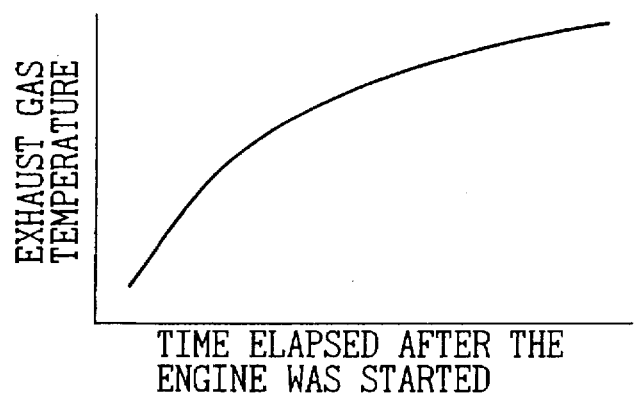
Figure 6C:
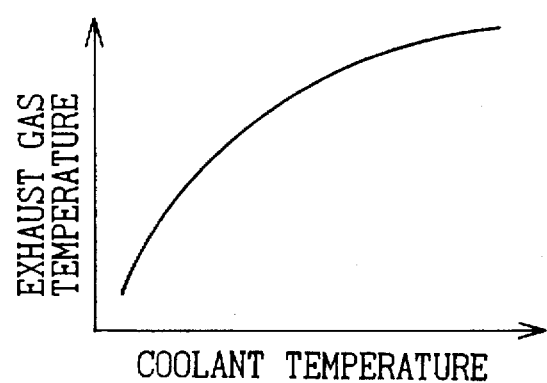

FIGS. 6A–6C are diagrams for explaining the relationship between the temperature of the exhaust gas and that of the coolant temperatures, and FIG. 6A shows how the coolant temperature changes after the engine is started, and FIG. 6B shows how the temperature of the exhaust gas changes after the engine is started.

FIG. 6C shows a graph into which FIG. 6A and FIG. 6B are combined, plotting the coolant temperature along the abscissa and the exhaust gas temperature along the ordinate. As shown, the exhaust gas temperature after the engine is started up can be expressed as a function of the coolant temperature after the engine is started up; that is, the auxiliary power $P_P$ can be expressed as a function that decreases as the coolant temperature $T_{hw}$ rises.

Further, since the amount of heat that the air-fuel ratio sensor has received is proportional to time elapsed after the engine has been started, the auxiliary power $P_P$ can be reduced as time elapses, and can be expressed as a function which decreases as time elapses after the engine has been started, that is, as the counter TS becomes large.

The routine is terminated after the auxiliary power $P_P$ is calculated as a function of the coolant temperature $T_{hw}$ and the counter TS by the following formula.

$$P_P = P_P(T_{hw}, TS)$$

Figure 7:
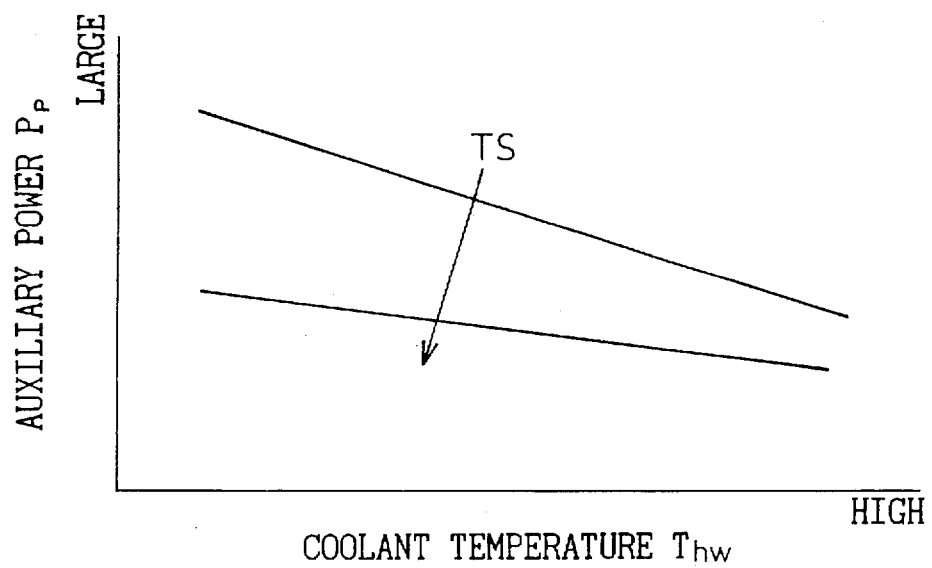
FIG. 7 is an auxiliary power calculating map.

FIG. 7 shows a map for determining the auxiliary power $P_P$, where the coolant temperature $T_{hw}$ is plotted along the abscissa and the auxiliary power $P_P$ along the ordinate. The parameter is the counter TS.

According to the above-described embodiment, it is possible to expedite the activation of the air-fuel ratio sensor while preventing the heater temperature from rising too high, regardless of the engine coolant temperature at the engine start-up.

However, the heater resistance is affected not only by the manufacturing tolerance, but also by age deterioration, and an interval while the electric power is supplied at the 100% duty ratio control is prolonged, because calorific power generated from the heater becomes small when the heater resistance is large. Therefore, the activation of the air-fuel ratio may be delayed because the auxiliary power $P_P$, after the 100% duty ratio control, is insufficient when the auxiliary power $P_P$ is determined in accordance with the time elapsed after the engine was started.

The second embodiment hereinafter described solves the above problem by calculating the auxiliary power $P_P$ as a function of the coolant temperature $T_{hw}$ and the time elapsed after completion of the 100% duty ratio control.

Figure 8:
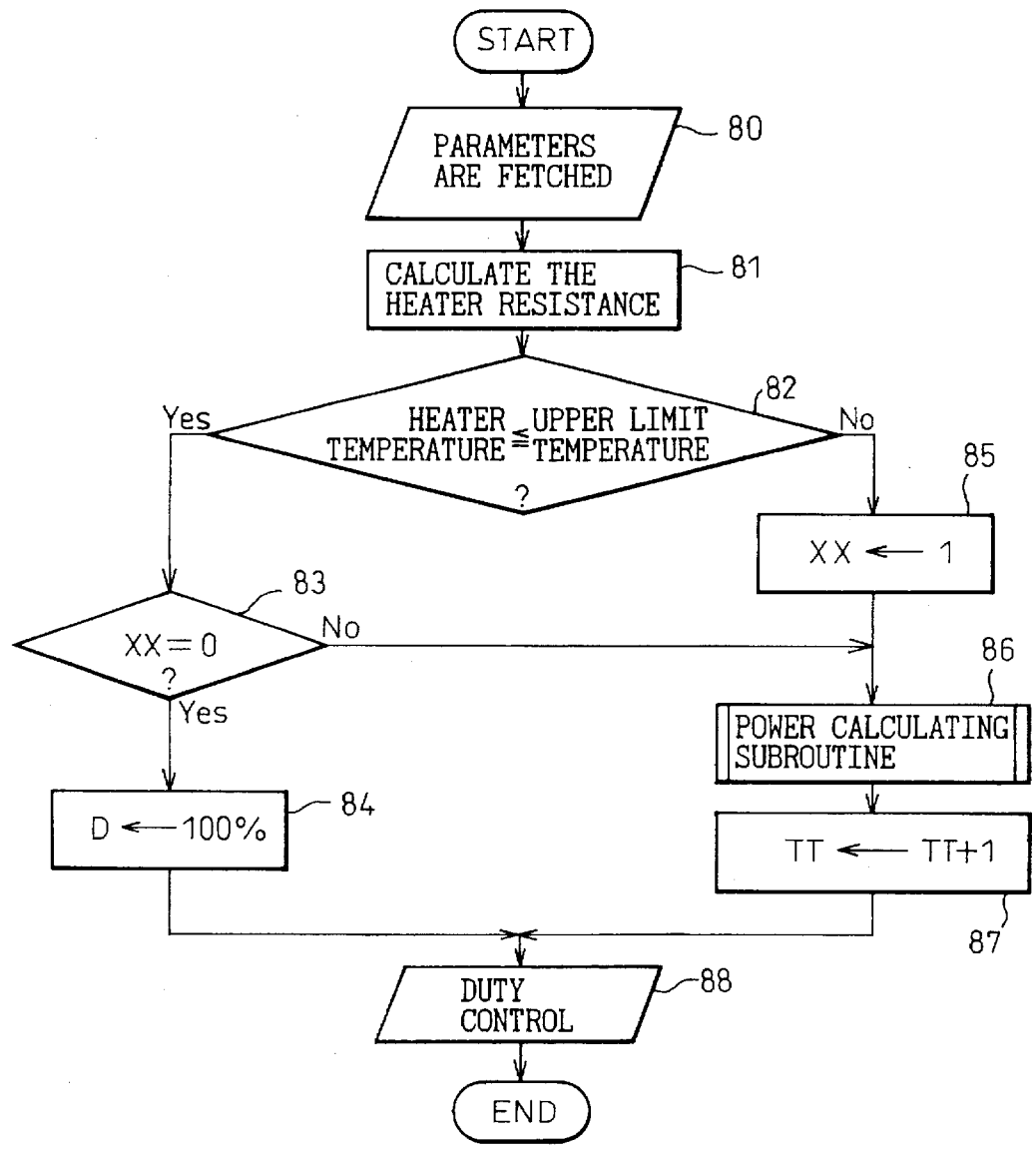
FIG. 8 is a flowchart of a second heater control routine.

FIG. 8 is a flowchart illustrating a second heater control routine which is executed in the controller 13. Compared with the first heater control routine, this routine includes an additional step for incrementing a counter that indicates the time elapsed after the heater temperature reaches the upper limit temperature. This routine is executed every prescribed interval.

An engine speed $N_e$, an intake pressure $P_M$, a voltage $V_h$ at the downstream of the heater, a current $I_h$ which flows through the heater, and a coolant temperature $T_{hw}$ are fetched.

At step 81, heater resistance $R_h$ is calculated from the battery voltage $V_B$, the voltage $V_h$ at the downstream of the heater, and the current $I_h$ which flows through the heater, using the following equation $$R_h = (V_B - V_h)/I_h$$

At step 82, it is determined whether or not the heater temperature is less than or equal to a predetermined upper limit temperature (for example, 1100° C.), that is, whether or not the heater resistance $R_h$ is less than or equal to an upper limit resistance corresponding to the upper limit temperature.

When the determination at step 82 is affirmative, that is, when the heater temperature is not higher than the upper limit temperature, the control proceeds to step 83 to determine whether or not the flag XX, indicating that the heater temperature has exceeded the upper limit temperature after the engine was started, is 0, that is, whether or not the heater temperature has ever risen above the upper limit temperature after the engine was started. Here, the flag XX was initialized to 0 by a not shown initialization routine when the engine was started.

When the determination at step 83 is affirmative, that is, if the heater temperature has never risen above the upper limit temperature after the engine was started, then the control proceeds to step 84, where the duty cycle D is set to 100% to expedite activation of the air/fuel ratio sensor 11. The control then proceeds to step 88.

Conversely, when the determination at step 82 is negative, that is, when the heater temperature is above the upper limit temperature, the control proceeds to step 85, where the flag XX is set to 1, and then the control proceeds to step 86. When the determination at step 83 is negative, that is, when the heater temperature has ever risen above the upper limit temperature after the engine was started, the control also proceeds to step 86.

The power calculation subroutine is executed at step 86, then the counter TT, which indicates the time elapsed after the heater reached the upper limit temperature, is incremented at step 87, and the control proceeds to step 88.

The switching element 122 is controlled using the duty cycle D determined in step 84 or step 86 at step 88, and then the routine is terminated.

The power calculation subroutine executed in step 86 is shown in FIG. 3.

Figure 9:
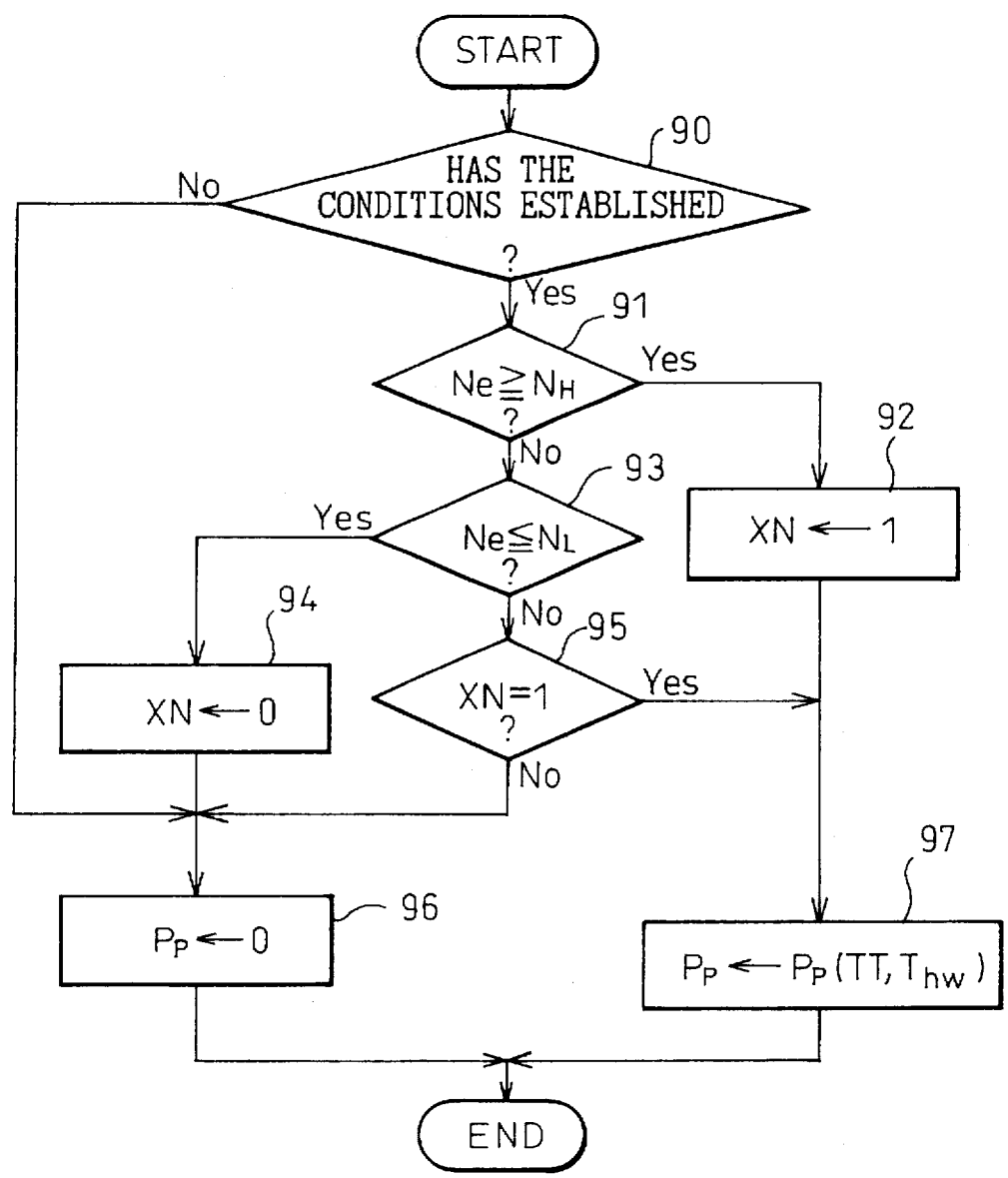
FIG. 9 is a flowchart of a second auxiliary power calculation routine.

FIG. 9 is a flowchart illustrating a second auxiliary power calculating routine executed in the controller 13. This routine eliminates the step of incrementing the counter indicating the elapsed time after the engine was started from the first auxiliary power calculating routine and the auxiliary power $P_P$ is calculated based on the coolant temperature $T_{hw}$ and the time elapsed after the heater reached the upper limit temperature. This routine is executed every prescribed interval.

At step 90, it is determined whether or not the conditions for calculating the auxiliary power are established. The conditions are the same as those described in the first auxiliary power calculating routine.

When the determination at step 90 is affirmative, that is, when the conditions for calculating the auxiliary power are established, the control proceeds to step 91.

Step 91 through step 95 concern the processing to determine whether or not an engine cranking has been completed. This is determined by determining whether or not the engine speed $N_e$ has exceeded cranking completion engine speed $N_H$ (for example, 400 rpm). To stabilize this determination, a hysteresis is applied.

At step 91, it is determined whether or not the engine speed $N_e$ has exceeded the cranking completion engine speed $N_H$. When the determination at step 91 is affirmative, that is, when the engine speed $N_e$ has exceeded the cranking completion engine speed $N_H$, cranking completion flag XN is set to 1 at step 92, and the control proceeds to step 97.

When the determination at step 91 is negative, the control proceeds to step 93, where it is determined whether or not the engine speed $N_e$ is less than or equal to the cranking incompletion engine speed $N_L$ (for example, 200 rpm).

When the determination at step 93 is affirmative, that is, when the engine speed $N_e$ is less than or equal to the cranking incompletion engine speed $N_L$, the cranking completion flag XN is set to 0 at step 94, and the control proceeds to step 96.

When the determination at step 93 is negative, that is, when the engine speed $N_e$ is above the cranking incompletion engine speed $N_L$ but not above the cranking completion engine speed $N_H$, the control proceeds to step 95 to determine whether or not the cranking completion flag XN is 1. When the determination is negative, the control proceeds to step 96, but when the determination is affirmative, the control proceeds to step 97.

At step 96, the correction power $P_P$ is set to 0.0, and the routine is terminated. Further, when the determination at step 90 is negative, that is, when the conditions for calculating the auxiliary power are not established, the control also proceeds to step 96.

The auxiliary power $P_P$ is calculated based on the coolant temperature $T_{hw}$, and the counter TT indicating the time elapsed after the heater reached the upper limit temperature at step 97 using the following formula.

$$P_P = P_P(TT, T_{hw})$$

After that, the routine is terminated.

In this case also, the auxiliary power $P_P$ calculation map shown in FIG. 7 can be used by using TT as the parameter.

In this way, according to the second embodiment, when the heater resistance becomes large, that is, when the time required to reach the upper limit temperature increases, the decrease of the auxiliary power $P_P$ and the delay in the air-fuel ratio sensor activation can be prevented.

We claim:

1. An apparatus for controlling a heater for heating an air-fuel ratio sensor installed in an exhaust pipe for detecting air-fuel ratio of exhaust gas, comprising:

an operating condition detecting means for detecting an operating condition of an internal combustion engine;

a base electric power determining means for determining a base electric power in accordance with the operating condition detected by said operating condition detecting means;

an auxiliary electric power determining means for determining an auxiliary electric power which becomes less as a coolant temperature of the engine detected by said operating condition detecting means becomes lower, and becomes less as the time elapsed since the engine was started becomes longer; and an electric power controlling means for controlling an electric power supplied to the heater by adding the auxiliary electric power determined by said auxiliary electric power determining means to the base electric power determined by said base electric power determining means.

2. An apparatus for controlling a heater for heating an air-fuel ratio sensor installed in an exhaust pipe for detecting air-fuel ratio of exhaust gas of claim 1, wherein;

said electric power controlling means continuously supplies the electric power before a resistance of the heater reaches a fixed resistance after the engine was started, and controls the electric power by adding the auxiliary electric power determined by said auxiliary electric power determining means to the base electric power determined by said base electric power determining means after the resistance of the heater reaches a fixed resistance.

3. An apparatus for controlling a heater for heating an air-fuel ratio sensor installed in an exhaust pipe for detecting air-fuel ratio of exhaust gas of claim 2, wherein;

said auxiliary electric power determining means determines an auxiliary electric power so that it becomes less as a coolant temperature of the engine detected by said operating condition detecting means becomes lower, and becomes less as the time elapsed since the resistance of the heater reached a fixed resistance becomes longer.

4. A method for controlling a heater for heating an air-fuel ratio sensor installed in an exhaust pipe for detecting air-fuel ratio of exhaust gas, comprising steps of:

an operating condition detecting step for detecting an operating condition of an internal combustion engine;

a base electric power determining step for determining a base electric power in accordance with the operating condition detected at said operating condition detecting step;

an auxiliary electric power determining step for determining an auxiliary electric power which becomes less as a coolant temperature of the engine detected at said operating condition detecting step becomes lower, and becomes less as the time elapsed since the engine was started becomes longer; and an electric power controlling step for controlling an electric power supplied to the heater by adding the auxiliary electric power determined at said auxiliary electric power determining step to the base electric power determined at said base electric power determining step.

5. A method for controlling a heater for heating an air-fuel ratio sensor installed in an exhaust pipe for detecting air-fuel ratio of exhaust gas of claim 4, wherein;

said electric power controlling step continuously supplies the electric power before a resistance of the heater reaches a fixed resistance after the engine was started, and controls the electric power by adding the auxiliary electric power determined at said auxiliary electric power determining step to the base electric power determined at said base electric power determining step after the resistance of the heater reaches a fixed resistance.

6. A method for controlling a heater for heating an air-fuel ratio sensor installed in an exhaust pipe for detecting air-fuel ratio of exhaust gas of claim 5, wherein;

said auxiliary electric power determining step determines an auxiliary electric power so that it becomes less as a coolant temperature of the engine detected at said operating condition detecting step becomes lower, and becomes less as the time elapsed since the resistance of the heater reached a fixed resistance becomes longer.

* * * * *